US006248754B1

(12) United States Patent
Coulton et al.

(10) Patent No.: US 6,248,754 B1
(45) Date of Patent: Jun. 19, 2001

(54) SUBSTITUTED ISOQUINOLINE DERIVATIVES AND THEIR USE AS ANTICONVULSANTS

(75) Inventors: Steven Coulton, Linton; Roderick Alan Porter, Baldock, both of (GB)

(73) Assignee: SmithKline Beecham, p.l.c., Brentford (GB)

(*) Notice: Subject to any disclaimer, the term of this patent is extended or adjusted under 35 U.S.C. 154(b) by 0 days.

(21) Appl. No.: 09/581,647

(22) PCT Filed: Dec. 16, 1998

(86) PCT No.: PCT/GB98/03785

§ 371 Date: Jun. 15, 2000

§ 102(e) Date: Jun. 15, 2000

(87) PCT Pub. No.: WO99/31068

PCT Pub. Date: Jun. 24, 1999

(30) Foreign Application Priority Data

Dec. 17, 1997 (GB) .................................................. 9726695

(51) Int. Cl.[7] ...................... C07D 217/02; C07D 409/12; A61K 31/47

(52) U.S. Cl. ............................................ 514/310; 546/143
(58) Field of Search .............................. 546/143; 514/310

(56) References Cited

U.S. PATENT DOCUMENTS 4,022,900  5/1977  Mathison ............................ 424/258

FOREIGN PATENT DOCUMENTS

WO 97/48683  12/1997  (WO).
WO 98/41508  9/1998  (WO).

OTHER PUBLICATIONS

Mathison, et al., "Synthesis and Hypotensive Properties of Tetrahydroisoquinolines", (1973), Journal of Medicinal Chemistry, vol. 16, No. 4, pp. 332–336.

Primary Examiner—Zinna Northington Davis
(74) Attorney, Agent, or Firm—Linda E. Hall; Stephen A. Venetianer; Charles M. Kinzig

(57) ABSTRACT

The present invention relates to substituted isoquinoline derivatives and their use as anticonvulsants.

13 Claims, No Drawings

SUBSTITUTED ISOQUINOLINE DERIVATIVES AND THEIR USE AS ANTICONVULSANTS

This is a 371 of International Application PCT/GB98/03785, filed Dec. 16, 1998, which claims benefit from the following Provisional Application: GB 97256695.1, filed Dec. 17, 1997.

This invention relates to novel compounds, to processes for preparing them, and to their use as therapeutic agents.

U.S. Pat. No. 4,022,900 (Marion) discloses benzamidoetrahydroisoquinolines having anti-hypertensive and vasodilator properties.

WO97/48683 (SmithKline Beecham) discloses that benzamide compounds of formula (A) below possess anticonvulsant activity and are therefore believed to be useful in the treatment and/or prevention of anxiety, mania, and related depression disorders.

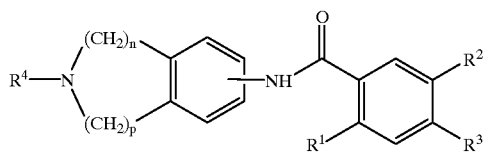

(A)

where n and p are independently integers from 1 to 4 and (n+p) is from 2 to 5;

$R^1$ is $C_{1-6}$allylO—;

$R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO_2$—, $(C_{1-4}$alkyl$)_2$NSO_2$— or $(C_{1-4}$alkyl$)$NHSO_2$—;

$R^3$ is hydrogen, halogen, $NO_2$, CN, $N_3$, trifluoromethyldiazirinyl, $C_{1-6}$alkylO—, $C_{1-6}$alkylS—, $C_{1-6}$alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —$NR^5R^6$ where $R^5$ is hydrogen or $C_{1-4}$alkyl, and $R^6$ is hydrogen, $C_{1-4}$alkyl, —CHO, —$CO_2C_{1-4}$alkyl or —$COC_{1-4}$alkyl;

$R^4$ is hydrogen, $C_{1-6}$alkyl, $C_{1-6}$alkenyl, or $C_{1-6}$alkynyl;

and also the compounds: N-(7-iodo-2-methyl-1,2,3,4-tetrahydroisoquinolin-5-yl)-5-benzoyl-2-methoxybenzamide, N-7-iodo-1,2,3,4-tetrahydroisoquinolin-5-yl)-5-benzoyl-2-methoxybenzamide, N-(5-iodo-1,2,3,4-tetrahydroisoquinolin-7-yl)-5-benzoyl-2-methoxybenzamide, N-(5-iodo-1,2,3,4-tetrahydroisoquinolin-7-yl)-2-methoxy-4-trifluoromethyldiazirinylbenzamide, N-(5-iodo-1,2,3,4tetrahydroisoquinolin-7-yl)-2-methoxy-5-trifluoromethyldiazirinyl-benzamide, N-(7-iodo-1,2,3,4-tetrahydroisoquinolin-5-yl)-2-methoxy-5-trifluoromethyldiazirinyl-benzamide and N-(8-fluoro-2-methyl-1,2,3,4-tetrahydroisoquinolin-5-yl)-4-t-butyl-2-methoxybenzamide.

It has now been surprisingly found that tetrahydroisoquinolinyl-carboxamide compounds of formula (I) below possess anti-convulsant activity and are believed to be useful in the for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Accordingly, the present invention provides a compound of formula (I) or pharmaceutically acceptable salt thereof:

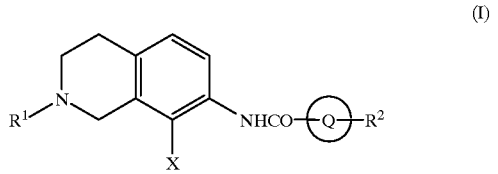

(I)

where Q is a monocyclic or bicyclic aryl or heteroaryl ring, $R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO_2$—, $R^2$ is hydrogen or up to three substituents selected from halogen, $NO_2$, CN, $N_3$, $CF_3O$, $CF_3S$—, $CF_3CO$—, tifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO_2$—, $(C_{1-4}$alkyl$)_2$NSO_2$—, $(C_{1-4}$alkyl$)$NHSO_2$—, $(C_{1-4}$alkyl$)_2$NCO—, $(C_{1-4}$alkyl$)$NHCO, $CONH_2$, $CF_3SO_2$, $C_{1-6}$alkenyl, $C_{1-6}$alkynyl or $C_{1-6}$hydroxyalkyl; or —$NR^3R^4$ where $R^3$ is hydrogen or $C_{1-4}$alkyl, and $R^4$ is hydrogen, $C_{1-4}$alkyl, formyl, —$CO_2C_{1-4}$alkyl or —$COC_{1-4}$alkyl; or two $R^2$ groups together form a carbocyclic ring that is saturated or unsaturated and unsubstituted or substituted by —OH or =O; and X is halogen, $C_{1-6}$alkoxy, $C_{1-6}$alkyl, $C_{2-6}$alkenyl optionally substituted by phenyl.

When compounds of the present invention possess chiral centres and as such may exist in different enantiomeric forms, the present invention extends to each enantiomeric form and mixtures thereof including diastereoisomers and racemates. Alkenyl compounds exist as geometric isomers and the present invention extends to each isomeric form and mixtures thereof.

The ring system Q is typically optionally substituted phenyl or optionally substituted thiophenyl. When two $R^2$ groups form a carbocyclic ring, this is typically a 5–7 membered ring, so that Q may be a naphthalene or an indane or indanone ring system.

In the formula (I), alkyl groups, including alkyl groups that are part of other moieties, such as alkoxy or acyl, may be straight chain or branched. Phenyl groups, including phenyl groups that are part of other moieties, in $R^2$ may optionally be substituted with one or more independently selected halogen or $C_{1-6}$alkyl, $C_{1-6}$alkoxy or $C_{1-6}$alkylcarbonyl. Suitable $C_{3-6}$cycloalkyl groups include cyclopropyl, cyclobutyl, cyclopentyl, and cyclohexyl. Suitable halo substituents include fluoro, chloro, iodo and bromo.

One suitable group of compounds of this invention are of formula (IA)

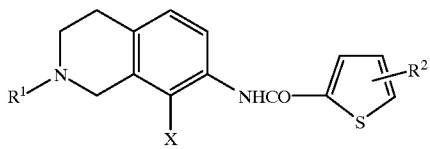

(IA)

and another suitable group are of formula (IB)

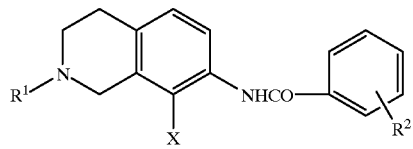

(IB)

A suitable group of compounds of formula (I) have
$R^1$ as hydrogen, methyl, ethyl, propyl, hydroxyethyl, formyl, acetyl, trifluoroacetyl or methanesulfonyl,
$R^2$ as hydrogen or one or more of methyl, ethyl, n-butyl, iso-propyl, t-butyl, phenyl, methoxy, ethoxy, isopropoxy, n-butoxy, cyclopropylmethoxy, phenoxy, benzyloxy, amino, acetylamino, nitro, azido, cyano, bromo, chloro, fluoro, iodo, acetyl, propionyl, pivaloyl, iso-butyroyl, benzoyl, iodobenzoyl, tifluoromethyl, perfluoroethyl, trifluoromethoxy, trifluoroacetyl, trifluoromethyldiazirinyl, methanesulfonyl, n-propylsulfonyl, isopropylsulfonyl, dimethylsulfamoyl, $CF_3SO_2$;
or two groups $R^2$ form a benzene, cyclopentane or cyclopentanone ring;
X as methyl, ethyl, chloro, bromo, iodo, fluoro, phenylethenyl.

A preferred group of compounds of formula (I) have
$R^1$ as hydrogen, methyl, hydroxyethyl, formyl or trifluoroacetyl.
$R^2$ as hydrogen or one or more of methyl, ethyl, iso-propyl, methoxy, ethoxy, isopropoxy, acetyl, propionyl, pivaloyl, cyano, bromo, chloro, fluoro, iodo, trifluoromethyl.
X as methyl, ethyl, chloro or bromo.

In a special class of compounds of formula (I), suitable for use as mechanistic probes, $R^2$ groups are photolabile groups, such as $N_3$, benzoyl and trifluoromethyldiazirinyl. Also radiolabels such as $^{125}I$ can be incorporated at R, and $^3H$ can be located at suitable positions.

Examples of compounds of formula (I) are:
N-(8-chloro-2-trifluoroacetyl-1,2,3,4-tetrahydroisoquinolin-7-yl)-3-bromo-4-ethoxybenzamide
N-(8-chloro-1,2,3,4-tetrahydroisoquinolin-7-yl)-3-bromo-4-ethoxybenzamide
N-(8-chloro-2-methyl-1,2,3,4-tetrahydroisoquinolin-7-yl)-3-bromo-4-ethoxybenzamide
N-(8-chloro-2-trifluoroacetyl-1,2,3,4-tetrahydroisoquinolin-7-yl)-4-methoxy-3-trifluoromethylbenzamide
N-(8-chloro-1,2,3,4-tetrahydroisoquinolin-7-yl)-4-methoxy-3-trifluoromethylbenzamide
N-(8-chloro-2-methyl-1,2,3,4-tetrahydroisoquinolin-7-yl)-4-methoxy-3-trifluoromethylbenzamide
N-(8-bromo-2-trifluoroacetyl-1,2,3,4-tetrahydroisoquinolin-7-yl)-4-methoxy-3-trifluoromethylbenzamide
N-(8-bromo-1,2,3,4-tetrahydroisoquinolin-7-yl)-4-methoxy-3-trifluoromethylbenzamide
N-(8-bromo-2-methyl-1,2,3,4-tetrahydroisoquinolin-7-yl)-4-methoxy-3-trifluoromethylbenzamide
N-(2,8-Dimethyl-1,2,3,4-tetrahydroisoquinolin-7-yl)-4-methoxy-3-trifluoromethylbenzamide
N-(2-(2-Hydroxyethyl)-8-chloro-1,2,3,4-tetrahydroisoquinolin-7-yl)-4-methoxy-3-trifluoromethylbenzamide
N-(2-formyl-8-chloro-1,2,3,4-tetrahydroisoquinolin-7-yl)-4-methoxy-3-trifluoromethylbenzamide
N-(8-ethyl-2-trifluoroacetyl-1,2,3,4-tetrahydroisoquinolin-7-yl)-4-methoxy-3-trifluoromethylbenzamide
N-(8-ethyl-1,2,3,4-tetrahydroisoquinolin-7-yl)-4-methoxy-3-trifluoromethylbenzamide
N-(8-ethyl-2-methyl-1,2,3,4-tetrahydroisoquinolin-7-yl)-4-methoxy-3-trifluoromethylbenzamide
N-(8-chloro-2-methanesulfonyl-1,2,3,4-tetrahydroisoquinolin-7-yl)-4-methoxy-3-trifluoromethylbenzamide
N-(8-Styryl-2-trifluoroacetyl-1,2,3,4-tetrahydroisoquinolin-7-yl)-4-methoxy-3-trifluoromethylbenzamide
N-(8-Styryl-1,2,3,4-tetrahydroisoquinolin-7-yl)-4-methoxy-3-trifluoromethylbenzamide
N-(8-Styryl-2-methyl-1,2,3,4-tetrahydroisoquinolin-7-yl)-4-methoxy-3-trifluoromethylbenzamide hydrochloride
N-(8-Bromo-2-trifluoroacetyl-1,2,3,4-tetrahydroisoquinolin-7-yl)-3-acetyl-4-ethoxybenzamide
N-(8-Bromo-1,2,3,4-tetrahydroisoquinolin-7-yl)-3-acetyl-4-ethoxybenzamide
N-(8-Chloro-1,2,3,4-tetrahydroisoquinolin-7-yl)-3-fluoro-4-methoxybenzamide
N-(8-Chloro-1,2,3,4-tetrahydroisoquinolin-7-yl)-3-chloro-4-ethoxybenzamide
N-(8-Chloro-1,2,3,4-tetrahydroisoquinolin-7-yl)-3-bromo-4-methoxybenzamide
N-(8-Chloro-1,2,3,4-tetrahydroisoquinolin-7-yl)-3-acetyl-4-ethoxybenzamide
N-(8-Chloro-1,2,3,4-tetrahydroisoquinolin-7-yl)-3-acetyl-4-iso-propoxybenzamide.

When synthesised, these compounds are often in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sublingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, or amyotrophic lateral sclerosis (ALS) which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, or amyotrophic lateral sclerosis (ALS) comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, or amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, or amyotrophic lateral sclerosis (ALS).

Another aspect of the invention is a process for the preparation of compounds of formula (I), which comprises reacting a compound of formula (II)

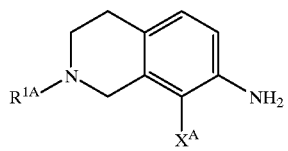

(II)

where $R^{1A}$ is $R^1$ as defined for formula (I) or a group convertible to $R^1$ and $X^A$ is X as defined in claim 1 or a group convertible to X with a compound of formula (III)

(III)

where Q is as defined in formula (I), Y is Cl or OH, and $R^{2A}$ groups are independently $R^2$ as defined for formula (I) or groups convertible to $R^2$, and where required converting an $X^A$, $R^{1A}$ or $R^{2A}$ group to an X, $R^1$ or $R^2$ group, converting one X, $R^1$ or $R^2$ group to another X, $R^1$ or $R^2$ group, converting a salt product to the free base or another pharmaceutically acceptable salt, or converting a free base product to a pharmaceutically acceptable salt.

Conventional conditions for condensation of amines with carboxylic acids or active derivatives thereof, such as acid chlorides, may be used. For example the amides and acids may be reacted in the presence of a mixture of ethyl (dimethylaminopropyl)-carbodiimide/hydroxybenzotriazole in a suitable solvent such as dimethyl formamide, and amines and acid chlorides may be reacted together in a suitable solvent such as ethyl acetate or dichloromethane, optionally in the presence of a base such as triethylamine.

Reaction of a compound of formula (III) which is an acid chloride (Y=Cl) typically results in formation of the hydrochloride salt of the compound of formula (I). Hydrochloride salts can also be obtained by passing HCl gas into a solution of the free base, or adding a solution of HCl in ether.

Conversions of an $R^{1A}$ or $R^{2A}$ group to a $R^1$ or $R^2$ group typically arise when a protecting group is needed during the above coupling reaction or during the preparation of the reactants by the procedures described below. Interconversion of one $R^1$ or $R^2$ group to another typically arises when one compound of formula (I) is used as the immediate precursor of another compound of formula (I) or when it is easier to introduce a more complex or reactive substituent at the end of a synthetic sequence.

Compounds of formula (II) may be prepared from a nitro-tetrahydroisoquinoline of formula (IV).

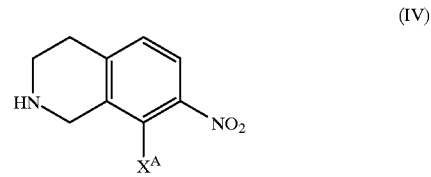

(IV)

by reaction with a compound $R^{1A}Z$ where Z is a leaving group such as halogen, especially iodo, or tosylate to obtain an intermediate of formula (V)

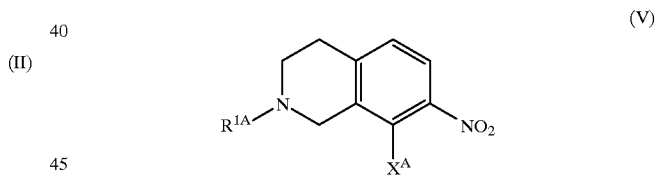

(V)

which can be hydrogenated, for example using either tin (II) chloride and HCL or hydrogen and a palladium/activated carbon catalyst, to obtain an amino-tetrahydroisoquinoline of formula (II).

When the intended $R^{1A}$ group is methyl, the compound of formula (IV) may also be reacted with formic acid and formaldehyde to introduce the N-methyl group.

The nitro-tetrahydroisoquinoline of formula (IV) in which $X^A$ is hydrogen may be prepared by hydrolysis of 2-trifluoroacetyl-7-nitro-tetrahydroisoquinoline obtained by reaction of an N-(nitrophenyl)ethyl-trifluoroacetamide and paraformaldehyde in acidic conditions using the procedure of Stokker, Tet. Lett., 1996, 37, 5453. N-(nitrophenyl)ethyl-trifluoroacetamides can be prepared from readily available materials by reaction of trifluoracetic anhydride with lutidine and nitrophenethylamine hydrochloride, as illustrated in the Descriptions below.

Compounds of formula (II) may also be prepared from the corresponding amino-isoquinoline (or its nitro-analogue) of formula (VI)

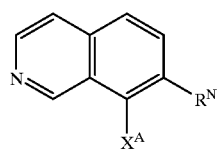
(VI)

where $R^N$ is $NH_2$ or $NO_2$
by reaction with a compound $R^{1A}Z$ where Z is a leaving group such as halogen, especially iodo, or tosylate to obtain an intermediate of formula (VII)

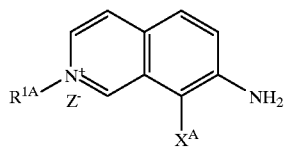

which can be reduced, for example using sodium borohydride, or hydrogenated, for example using hydrogen and a palladium/activated carbon catalyst, to obtain a tetrahydroisoquinoline of formula (It). When the compound of formula (VII) is replaced by a nitro-isoquinoline, the nitro group is converted to an amino group in the hydrogenation step.

When the intended $R^1$ is hydrogen, the N of the tetrahydroisoquinoline or isoquinoline is preferably protected conventionally, prior to the coupling step that forms the carboxamide of formula (I), for example by tert.-butoxycarbonyl or trifluoroacetyl. The compound can be deprotected under standard conditions, for example using trifluoroacetic acid/methylene chloride or potassium carbonate in aqueous methanol.

Amino/nitro-isoquinolines of formulae (VI) and the reagents used are commercially available, or can be prepared from commercially available materials using conventional procedures described in the literature.

The substituent $X^A$ may be a group X already present on commercially available starting materials usable in the above described procedures. When the substituent $X^A$ is a group convertible to X, then X may be introduced during any of the procedures above, for example by conventional substitution of the aromatic ring of compounds of formula (IV), (V) or (VII). Most suitably the substituent X as halogen is introduced to a compound of formula (II) in which $X^A$ is hydrogen. For example, X as halogen may be incorporated by reaction with a halo-succinimide as illustrated in the Descriptions below. As a further example, X as alkyl may be introduced by reaction of a compound of formula (II) in which X is bromo with an alkyl stannane, as illustrated in the Descriptions and Examples below. The compound of formula (II) in which X is bromo may be obtained by halogenation of an amino-tetrahydroisoquinoline of formula (II) in which $X^A$ is hydrogen with NBS, again using procedures illustrated in the Descriptions below.

Compounds of formula (III) may be prepared by further substitution of commercially available benzoic acid or thiophene carboxylic acid derivatives using conventional procedures, or by oxidation of corresponding substituted benzyl alcohols. Alternatively benzoic acids can be prepared from correspondingly substituted phenols, for example by formation of the acetate, conversion to an acetophenone and then to the desired acid. Examples of these procedures are documented in WO 98/41507 and WO98/41508.

Where the above described intermediates are novel compounds, they also form part of this invention.

The preparation of compounds of this invention is further illustrated by the following Descriptions and Examples. The utility of compounds of this invention is shown by the Pharmacological Data that follow the Examples.

Description 1
N-2-(4-Nitrophenyl)ethyl-trifluoroacetamide

A solution of trifluoroacetic anhydride (10.6 ml) in dichloromethane (100 ml) was added dropwise to a stirred solution of 2,6-lutidine (17.44 ml) and 4-nitrophenethylamine hydrochloride (15.2 g; 75 mmol) at 0° C. The mixture was stirred at 25° C. overnight under argon and then washed with dilute citric acid (×2), brine and dried over $Na_2SO_4$. The material in the organic phase gave the tide compound D1 as a pale yellow solid (19.04 g).

Description 2
7-Nitro-1,2,3,4-tetrahydro-2-trifluoracetylisoquinoline

The compound D1 (2.26 g; 9.15 mmol) and paraformaldehyde (0.45 g; 14.4 mmol) in acetic acid (10 ml) and conc. $H_2SO_4$ (15 ml) were stirred at 25° C. for 20 h according to the procedure of G. E. Stokker., Tet. Lett., 1996, 37, 5453. Work up afforded the title compound D2 as a white solid (2.17 g).

$^1$H NMR (CDCl$_3$) δ: 3.10 (2H, m), 3.92 (2H, m), 4.85+ 4.92 (2H, 2×s), 7.38 (1H, t), 8.10 (2H, m); m/z (EI): 274 (M$^+$)

Description 3
7-Nitro-1,2,3,4-tetrahydroisoquinoline

The compound D2 (17.22 g; 63 mmol) was hydrolysed at room temperature using a solution of potassium carbonate (46.6 g) in 10% aqueous methanol (660 ml). Work-up with dichloromethane gave the title compound (11 g).

Description 3
7-Amino-1,2,3,4-tetrahydro-2-trifluoroacetylisoquinoline

The 7-nitro compound D2 (0.99 g; 3.6 mmol) in ethanol (50 ml) was hydrogenated over 10% palladium on carbon (450 mg) at atmospheric pressure for 4 h. The catalyst was removed by filtration through a pad of Celite and evaporation in vacuo gave the title compound as a white solid (840 mg).

$^1$H NMR (250 MHz, CDCl$_3$) δ: 2.84 (2H, t), 3.23 (2H, br s), 3.82 (2H, m), 4.66 (2H, d, restricted rotation around C–1), 6.47 (1H, m), 6.57 (1H, m), 6.96 (1H, m)

Description 4
7-Amino-8-chloro-1,2,3,4-tetrahydro-2-trifluoroacetylisoquinoline

To a solution of amine D3 (1.00 g) in acetonitrile (20 ml) N-chlorosuccinimide (0.60 g) was added and the solution stirred at room temperature for 6 days. The solution was diluted with ethyl acetate, washed with water and the organic phase dried (MgSO$_4$) and solvent removed at reduced pressure. The residue was column chromatographed (silica gel, dichloromethane then 2% methanol/dichloromethane) to give 7-amino-8-chloro-1,2,3,4-tetrahydro-2-trifluoroacetyl-isoquinoline (0.72 g) as a pale yellow solid.

$^1$H NMR (250 MHz, CDCl$_3$) δ: 2.85 (2H, m), 3.83 (2H, dt, restricted amide rotation), 4.76 (2H, s), 6.68 (1H, m) and 6.89 (1H, m).

Description 5
7-Amino-8-bromo-1,2,3,4-tetrahydro-2-trifluoroacetyl-isoquinoline

The title compound (0.27 g) was prepared from amine D3 (0.24 g) and N-bromosuccinimide (0.20 g) according to the method of Description 4.

$^1$H NMR (250 MHz, CDCl$_3$) δ: 2.85 (2H, m), 3.76–3.87 (2H, m, restricted amide rotation), 4.72 (2H, d due to restricted amide rotation), 6.68 (1H, m) and 6.93 (1H, m).

Preparation 1
3-Bromo-4-ethoxybenzoic acid

To a solution of 4ethoxybenzoic acid (3.6 g, 0.022 mol) in chloroform (60 ml) was added bromine (1.13 ml, 0.022 mol) in chloroform (20 ml) dropwise. After stirring overnight at room temperature the precipitate was filtered off and dried to afford the title compound as a white solid.

$^1$H NMR (DMSO-D$_6$) δ: 1.45 (3H, t, J=7 Hz), 4.26 (2H, q, J=7 Hz), 7.26 (1H, d, J=9 Hz), 7.98 (1H, dd, J=2, 9 Hz), 8.12 (1H, d, J=2 Hz)

Preparation 2
4-Methoxy-3-trifluoromethylbenzoic acid

3-Bromo-4-ethoxybenzoic acid methyl ester (1.4 g; 5.4 mmol) in DMF (25 ml) and toluene (8 ml) under argon was treated with potassium trifluoroacetate (1.53 g; 10.1 mmol) and copper (I) iodide (2.1 g, 10.9 mmol). The mixture was heated to 170° C. with removal of water (Dean/Stark), and then at 155° C. overnight. The mixture was allowed to cool, poured into ether and water and filtered through Kieselguhr. The organic layer was dried (Na$_2$SO$_4$) and concentrated in vacuo to give a brown solid. Chromatography on Kieselgel 60 with 1:1 ether/petrol gave a solid which was hydrolysed in 1:1 methanolic: aqueous NaOH 50 ml) at 50° C. Work-up gave the title compound as a white solid (1 g).

$^1$H NMR (DMSO-D$_6$) δ: 3.78 (3H, s), 7.18 (1H, d, J=9 Hz), 7.90 (1H, d, J=2 Hz), 8.00 (1H, dd, J=2, 9 Hz), 12.70–13.10 (1H, br, exchangeable)

Preparation 3
4-Methoxy-3-trifluoromethylbenzoyl chloride

The title compound was prepared from 4-methoxy-3-trifluoromethylbenzoic acid with oxalyl chloride and DMF in chloroform at room temperature [D. Levin, Chem. Br., 1977, 20] followed by evaporation in vacuo.

Preparation 4
3-Chloro-4-ethoxybenzoic acid $^1$H NMR (DMSO-D$_6$) δ: 1.39 (3H, t, J=7 Hz), 4.20 (2H, q, J=7 Hz), 7.22 (1H, d, J=7 Hz), 7.87 (2H, m).

Preparation 5
Methyl 3-Bromo-4-iso-propoxybenzoate

Methyl 3-bromo-4-hydroxybenzoate (2.5 g, 10.8 mmol) in DMF (35 ml) was treated with potassium carbonate (3.0 g, 21.6 mmol), 2-iodopropane (2.76, 21.6 mmol) and then stirred at 25° C. for 48 h. Work-up with ethyl acetate gave the title compound (3.0 g).

$^1$H NMR (250 MHz, CDCl$_3$) δ: 1.41 (6H, d, J=7 Hz), 3.89 (3H, s), 4.66 (1H, m), 6.90 (1H, d, J=8 Hz), 7.93 (1H, dd, J=8, 2 Hz), 8.22 (1H, d, J=2 Hz)

Preparation 6
Methyl 3-Acetyl-4-iso-propoxybenzoate

The bromo ester P5 (2.5 g, 8.3 mmol) in dry dioxan (30 ml) was treated with (1-ethoxyvinyl)-tributyl tin (3.58 g, 9.9 mmol) followed by tetrakis triphenylphosphine palladium (o) (0.48 g, 0.4 mmol) and heated at 100° for 18 h. After cooling, the mixture was acidified and aqueous work-up and extraction into ethyl acetate gave a coloured oil (5.6 g). Flash chromatography on Kieselgel 60 [hexane to 20% EtAc/hexane gave the title compound as a yellow oil (2.3 g).

Preparation 7
3-Acetyl-4-iso-propoxybenzoic acid

Saponification of the ester P6 (2.3 g) gave the title compound as a white solid (1.3 g).

$^1$H NMR (250 MHz, CDCl$_3$) δ: 1.48 (6H, d, J=7 Hz), 2.63 (3H, s), 4.80 (1H, m), 7.00 (1H, d, J=8 Hz), 8.17 (1H, dd, J=8, 2 Hz), 8.46 (1H, d, J=2 Hz)

Preparation 8
3-Acetyl-4-ethoxybenzoic acid

Prepared in a similar maimer to that described for Preparations 6 and 7.

$^1$H NMR (250 MHz, CDCl$_3$) δ: 1.53 (3H, t, J=7 Hz), 2.65 (3H, s), 4.23 (2H, q, J=7 Hz), 7.01 (1H, d, J=8 Hz), 8.19 (1H, dd, J=8, 2 Hz), 8.48 (1H, d, J=2 Hz).

EXAMPLE 1

N-(8-Chloro-2-trifluoroacetyl-1,2,3,4-tetrahydroisoquinolin-7-yl)-3-bromo-4-ethoxybenzamide To a solution of amine D4 (0.28 g) in tetrahydrofuran (5 ml) containing triethylamine (0.21 ml), 3-bromo-4-ethoxybenzoyl chloride (0.37 g) in tetrahydrofuran (7 ml) was added. The mixture was stirred overnight partitioned between ethyl acetate and water and the organic phase dried (MgSO$_4$) and solvent removed at reduced pressure. The residue was purified by column chromatography (silica gel, and an ethyl acetate/hexane gradient to give after combining of appropriate fractions the title compound (0.31 g) as a colourless solid.

$^1$H NMR (250 MHz, CDCl$_3$) δ: 1.26 (3H, t), 2.98 (2H, m), 3.85 (2H, dt, restricted amide rotation), 4.11 (2H, q), 4.80 (2H, d due to restricted amide rotation) 6.98 (1H, d), 7.18 (1H, t), 7.84 (1H, dd), 8.14 (1H, d), 8.28 (1H, m) and 8.39 (1H, d); m/z (API): 507 (MH$^+$; 100%)

EXAMPLE 2

N-(8-Chloro-1,2,3,4-tetrahydroisoquinolin-7-yl)-3-bromo-4-ethoxybenzamide

A solution of N-(8-chloro-2-trifluoroacetyl-1,2,3,4-tetrahydroisoquinolin-7-yl)-3-bromo-4-ethoxybenzamide (0.28 g) in methanol/water (5 ml 9:1) was treated with potassium carbonate (0.38 g) and stirred 12 h. The mixture was diluted with dichloromethane and washed with water. The organic phase was dried (MgSO$_4$) solvent removed at reduced pressure. The residue was chromatographed (silica gel, dichloromethane/methanol/ammonia up to 9:1:0.1 eluant) to give the title compound (0.18 g) as a colourless solid.

$^1$H NMR (250 MHz, CDCl$_3$) δ: 1.52 (3H, t), 2.79 (2H, t), 3.11 (2H, t), 4.04 (2H, s) 4.20 (2H, q) 6.96 (1H, d, J=6 Hz), 7.09 (1H, d, J=8.5 Hz), 7.84 (1H, dd, J=8.5, 2 Hz), 8.13 (1H, d, J=2 Hz), 8.26–8.29 (2H, m); m/z (API): 409, 411 (MH$^+$; 100%)

EXAMPLE 3

N-(8-chloro-2-methyl-1,2,3,4-tetrahydroisoquinolin-7-yl)-3-bromo-4-ethoxybenzamide A solution of N-(8-Chloro-1,2,3,4-tetrahydroisoquinolin-7-yl)-3-bromo-4-ethoxybenzamide (0.12 g) in 37% aqueous formaldehyde (0.63 ml) and formic acid (0.34 ml) and stirred at 80° C. for 3 h. Solid sodium hydroxide was added to neutralise the solution and the aqueous phase extracted with dichloromethane. The combined organic extracts were dried (MgSO$_4$) and solvent removed in vacuo to give the title compound (0.11 g).

$^1$H NMR (250 MHz, CDCl$_3$) δ: 1.52 (3H, t), 2.52 (3H, s), 2.68 (2H, t), 2.93 (2H, t), 3.61 (2H, s), 4.18 (2H, q), 6.96 (1H, d, J=6 Hz), 7.10 (1H, d, J=8.5 Hz), 7.84 (1H, dd, J=8.5, 2 Hz), 8.13 (1H, d, J=2 Hz), 8.25–8.28 (2H, m); m/z (API): 423, 425 (MH$^+$; 100%)

EXAMPLE 4

N-(8-Chloro-2-trifluoroacetyl-1,2,3,4-tetrahydroisoquinolin-7-yl)-4-methoxy-3-trifluoromethylbenzamide The title compound (0.32 g) was prepared from amine D4 (0.28 g) and 4-methoxy-3-trifluoromethylbenzoyl chloride (0.33 g) according to the procedure of Example 1.

¹H NMR (250 MHz, CDCl₃) δ: 2.99 (2H, m), 3.85 (2H, dt, restricted amide rotation), 4.81 (2H, d due to restricted amide rotation) 7.12–7.21 (2H, m), 8.08 (1H, d), 8.16 (1H, s), 8.28–8.40 (2H, m); m/z (API): 481 (MH⁺; 100%)

EXAMPLE 5

N-(8-Chloro-1,2,3,4-tetrahydroquinolin-7-yl)-4-methoxy-3-trifluoromethylbenzamide The title compound (0.05 g) was prepared from N-(8-chloro-2-trifluoroacetyl-1,2,3,4-tetrahydroisoquinolin-7-yl)-3methoxy-3-tifluoromethylbenzamide (0.29 g) according to the procedure of Example 2.

¹H NMR (250 MHz, CDCl₃) δ: 2.79 (2H, t), 3.11 (2H, t), 4.00 (3H, s), 4.05 (2H, s), 7.11 (2H, t), 8.09 (1H, d), 8.16 (1H, s), 8.26 (1H, d) and 8.31 (1H, br. s); m/z (API): 385 (MH⁺; 100%)

EXAMPLE 6

N-(8-Chloro-2-methyl-1,2,3,4-tetrahydroisoquinolin-7-yl)-4-methoxy-3-trifluoromethylbenzamide The title compound (0.13 g) was prepared from N-(8-chloro-1,2,3,4-tetrahydroisoquinolin-7-yl)-4-methoxy-3-trifluoromethylbenzamide (0.19 g) according to the procedure of Example 3.

¹H NMR (250 MHz, CDCl₃) δ: 2.53 (3H, s), 2.68 (2H, t), 2.92 (2H, t), 3.61 (2H, s) 4.00 (3H, s), 7.12 (2H, d), 8.09 (1H, d), 8.15 (1H, s), 8.26 (1H, d) and 8.29 (1H, br. s); m/z (API): 385 (MH⁺; 100%)

EXAMPLE 7

N-(8-Bromo-2-trifluoroacetyl-1,2,3,4-tetrahydroisoquinolin-7-yl)-4-methoxy-3-trifluoromethylbenzamide The title compound (0.32 g) was prepared from amine D5 (0.22 g) and 4methoxy-3-trifluoromethylbenzoyl chloride (0.22 g) according to the procedure of Example 1.

¹H NMR (250 MHz, CDCl₃) δ: 2.94–3.01 (21, m), 3.82–3.93 (2H, m, restricted amide rotation), 4.01 (3H, s), 4.78 (2H, d due to restricted amide rotation) 6.95 (1H, d), 7.14 (1H, d), 8.04 (1H, d), 8.18 (1H, s), 8.36 (1H, d) and 8.39 (1H, s); m/z (API): 524, 526 (MH⁺; 100%).

EXAMPLE 8

N-(8-Bromo-1,2,3,4-tetrahydroisoquinolin-7-yl)-4-methoxy-3-trifluoromethylbenzamide The title compound (0.12 g) was prepared from N-(8-bromo-2-trifluoroacetyl-1,2,3,4-tetrahydroisoquinolin-7-yl)-4methoxy-3-trifluoromethylbenzamide (0.24 g) according to the procedure of Example 2.

¹H NMR (250 MHz, CDCl₃) δ: 2.79 (2H, t), 3.11 (2H, t), 4.00 (5H, s), 7.13 (2H, dd), 8.10 (1H, dd, J=2.3 and 8.7 Hz) 8.18 (1H, d, 32.1 Hz), 8.25 (1H, d, J=8.5 Hz) and 8.38 (1H, s); m/z (API): 429, 431 (MH⁺; 100%)

EXAMPLE 9

N-(8-Bromo-2-methyl-1,2,3,4-tetrahydroisoquinolin-7-yl)-4-methoxy-3-trifluoromethylbenzamide The title compound (0.08 g) was prepared from N-(8-bromo-1,2,3,4-tetrahydroisoquinolin-7-yl)-4-methoxy-3-trifluoromethylbenzamide (0.09 g) according to the procedure of Example 3.

¹H NMR (250 MHz, CDCl₃) δ: 2.53 (3H, s), 2.67 (2H, t), 2.94 (2H, t), 3.59 (2H, s), 4.00 (3H, s), 7.15 (2H, t), 8.11 (1H, dd) 8.18 (1H, d), 8.25 (1H, d, J=8.5 Hz) and 8.37 (1H, s); m/z (API): 443, 445 (MH⁺; 100%)

EXAMPLE 10

N-2,8-Dimethyl-1,2,3,4-tetrahydroisoquinolin-7-yl)-4-methoxy-3-trifluoromethylbenzamide a) N-(8-Bromo-2-trifluoroacetyl-1,2,3,4-tetrahydroisoquinolin-7-yl)-3-methoxy-3-trifluoromethylbenzamide (0.25 g), was combined with lithium chloride (0.06 g), tetramethyltin (0.08 ml) and bis(triphenylphosphine)palladium(II)chloride (0.025 g) in dimethylformamide (5 ml) and the mixture warmed to 100° C. for 24 h. Solvent was removed at reduced pressure, filtered (Celite pad) and the filtrate column chromatographed (silica gel, diethyl ether eluant) to give N-(8-methyl-2-trifluoroacetyl-1,2,3,4-tetrahydroisoquinolin-7-yl)-4methoxy-3-trifluoromethylbenzamide (0.16 g).

¹H NMR (CDCl₃) δ: 2.31 (3H, m), 2.95–2.99 (2H, m), 3.81–3.90 (2H, m), 4.07 (3H, s), 4.70, 4.73 (2H, s, appears as 2 singlets due to restricted rotation), 7.04–7.12 (2H, m), 7.41–7.47 (1H, m), 7.63 (1H, br. s.), 8.08–8.11 (2H, m); m/z (API⁺): 461 (MH⁺)

b) N-(8-Methyl-2-trifluoroacetyl-1,2,3,4-tetrahydroisoquinolin-7-yl)-4-methoxy-3-trifluoromethylbenzamide (0.15 g) in methanol: 2N sodium hydroxide (15 ml 2:1) was stirred at room temperature for 1 h. 2M hydrochloric acid (4.5 ml) was added and solvent (10 ml) removed at reduced pressure. The residual solvent was extracted with dichloromethane, the organic phase washed with brine, dried MgSO₄) and solvent removed at reduced pressure to give N-(8-methyl-1,2,3,4-tetrahydroisoquinolin-7-yl)-4-methoxy-3-trifluoromethylbenzamide (0.08 g)

¹H NMR (CDCl₃) δ: 2.31 (3H, m), 2.07 (3H, s), 2.80 (2H, t), 3.09 (2H, t), 3.95 (2H, s), 3.98 (3H, s), 6.98 (1H, d), 7.09 (1H, d), 7.32 (1H, s), 7.69 (1H, br. s.), 8.07–8.10 (2H, m); m/z (API⁺): 365 (MH⁺)

c) The title compound (0.03 g) was prepared from N-(8-methyl-1,2,3,4-tetrahydroisoquinolin-7-yl)-4methoxy-3-trifluoromethylbenzamide (0.08 g), according to the method of Example 3.

¹H NMR (CDCl₃) δ: 2.01 (3H, s), 2.48 (3H, s), 2.68 (2H, t), 2.95 (2H, t), 3.48 (2H, s), 3.99 (3H, s), 7.00 (1H, d), 7.09 (1H, d), 7.30 (1H, d), 7.92 (1H br. s.), 8.08 (1H, br. s.), 8.11 (1H, br. s.); m/z (API⁺): 379 (MH⁺)

EXAMPLE 11

N-(2-(2-Hydroxyethyl)-8-chloro-1,2,3,4-tetrahydroisoquinolin-7-yl)-4-methoxy-3-trifluoromethylbenzamide a) A mixture of N-(8-chloro-1,2,3,4-tetrahydroisoquinolin-7-yl)-4-methoxy-3-trifluoromethylbenzamide (0.192 g) and 2-bromoethoxy-tert-butyldimethylsilane (0.24 g) were combined in dimethylformamide and warmed to 80° C. for 18 h. Solvent was removed at reduced pressure, the residue dissolved in dichloromethane and washed with saturated sodium hydrogen carbonate. The organic phase was dried (MgSO₄) and solvent removed at reduced pressure. The residue was column chromatographed (silica gel, ammonia/methanol/dichloromethane mixtures as eluant) to give N-(2-(2-tert-butyldimethylsilyloxyethyl)-8-chloro-1,2,3,4-tetrahydroisoquinolin-7-yl)-4-methoxy-3-trifluoromethylbenzamide (0.09 g)

b) N-(2-(2-Tert-butyldimethylsilyloxyethyl)-8-chloro-1,2,3,4-tetrahydroisoquinolin-7-yl)-4-methoxy-3- trifluoromethylbenzamide (0.09 g) in tetrahydrofuran (10 ml) was treated with tetrabutylammonium fluoride in tetrahydrofuran (1M, 0.16 ml) at room temperature overnight. The reaction mixture was diluted with ethyl acetate, washed with water, the organic phase dried ($MgSO_4$) and solvent removed at reduced pressure. The residue was column chromatographed (silica gel, ammonia/methanol/dichloromethane mixtures as eluant) to give the title compound (0.04 g)

$^1$H NMR $CDCl_3$) δ: 2.80 (4H, m), 2.91 (2H, m), 3.73 (2H, s), 3.75 (2H, t), 3.99 (3H, s), 7.11 (2H, dd), 8.07 (1H, dd), 8.16 (1H, d), 8.25 (1H, d) and 8.32 (1H, br. s.); m/z ($API^+$): 429 ($MH^+$)

EXAMPLE 12

N-(2-Formyl-8-chloro-1,2,3,4-tetrahydroisoquinolin-7-yl)-4-methoxy-3-trifluoromethylbenzamide Formic acetic anhydride (0.21 g) was added to N-(8-chloro-1,2,3,4-tetrahydroisoquinolin-7-yl)-4-methoxy-3-trifluoromethylbenzamide (0.15 g) and dimethylaminopyridine (0.05 g) in dichloromethane. The mixture was stirred at room temperature overnight and quenched with saturated aqueous sodium hydrogen carbonate (20 ml). The organic phase was separated and washed with brine, dried ($MgSO_4$) and solvent removed at reduced pressure. The residue was column chromatographed (silica gel, ammonia/methanol/dichloromethane mixtures as eluant) to give the title compound (0.10 g)

$^1$H NMR ($d^6$-DMSO, 353° K.) δ: 3.79 and 2.90 (2II, t, rotamers), 3.68 (2H, m), 3.99 (3H, s), 4.55 and 4.62 (2H, s, rotamers), 7.23 (1H, d), 7.39 (1H, d), 7.44 (1H, d), 8.21, 8.27, 8.32 (3H, s), 10.20 (1H, s); m/z ($API^+$): 413 ($MH^+$)

EXAMPLE 13

N-(8-Ethyl-2-trifluoroacetyl-1,2,3,4-tetrahydroisoquinolin-7-yl)-4-methoxy-3-trifluoromethylbenzamide N-(8-Bromo-2-trifluoroacetyl-1,2,3,4-tetrahydroisoquinolin-7-yl)-4-methoxy-3-trifluoromethylbenzamide (0.525 g), lithium chloride (0.127 g), tetraethyltin (0.47 g) and bis(triphenylphosphine)palladium(II)chloride (0.04 g) were combined in dimethylformamide (10 ml) and the mixture stirred under argon at 120° C. for 20 h. Solvent as removed at reduced pressure, the residue dissolved in dichloromethane and filtered through Celite. Solvent was removed at reduced pressure and the residue column chromatographed (silica gel, ethyl acetate/hexane mixtures) to give the title compound (0.18 g) as an oil.

$^1$H NMR ($CDCl_3$) δ: 1.24 (3H, t), 2.66 (2I, m), 2.99 (2H, m), 3.84 (2H, m), 4.00 (3H, s), 4.77 and 4.82 (2H, s, rotamers), 7.10 (2H, m), 7.62 (2H, m), 8.08 (2H, m); m/z ($API^+$): 475 ($MH^+$)

EXAMPLE 14

N-(8-Ethyl-1,2,3,4-tetrahydroisoquinolin-7-yl)-4-methoxy-3-trifluoromethylbenzamide N-(8-Ethyl-2-trifluoroacetyl-1,2,3,4-tetrahydroisoquinolin-7-yl)-4methoxy-3-trifluoromethylbenzamide (0.157 g) was dissolved in methanol/water (5:1 6 ml), potassium carbonate (0.228 g) added and the mixture stirred overnight. The mixture was partitioned between dichloromethane and water the organic phase separated and solvent removed at reduced pressure. The residue was column chromatographed (silica gel, ammonia/methanol/dichloromethane mixtures as eluant) to give the title compound (0.97 g)

$^1$H NMR ($CDCl_3$) δ: 1.15 (3H, t), 2.57 (2H, q), 2.82 (2H, t), 3.10 (2H, t), 3.99 (3H, s), 4.04 (2H, s), 7.00 (1H, d), 7.10 (1H, d), 7.49 (1H, d), 7.62 (1H, br. s.), 8.05–8.10 (2H, m); m/z ($API^+$): 379 ($NM^+$)

EXAMPLE 15

N-(8-Ethyl-2-methyl-1,2,3,4-tetrahydroisoquinolin-7-yl)-4-methoxy-3-trifluoromethylbenzamide The title compound (0.08 g) was prepared from N-(8-ethyl-1,2,3,4-tetrahydroisoquinolin-7-yl)-4-methoxy-3-trifluoromethylbenzamide (0.08 g) according to the method of Example 3.

$^1$H NMR ($CDCl_3$) δ: 1.17 (3H, t), 2.56 (3H, s), 2.57 (2H, q), 2.68 (2H, t), 2.95 (2H, m), 3.61 (2H, s), 3.99 (3H, s), 7.04 (1h, d), 7.10 (1H, d), 7.51 (1H, d), 7.59 (1H, s), 8.04–8.09 (2H, m); m/z ($API^+$): 393 ($MH^+$)

EXAMPLE 16

N-(8-Chloro-2-methanesulfonyl-1,2,3,4-tetrahydroisoquinolin -7-yl)-4-methoxy-3-trifluoromethylbenzamide N-(8-Chloro-1,2,3,4-tetrahydroisoquinolin-7-yl)-4-methoxy-3-trifluoromethylbenzamide (0.193 g) in dichloromethane (10 ml) containing triethylamine (0.055 ml) was treated with methanesulfonyl chloride ((0.063 g) and the mixture stirred for 48 h. Water was added and the organic phase separated and solvent removed at reduced pressure. The residue was triturated with diethyl ether to give the title compound (0.19 g).

$^1$H NMR ($CDCl_3$) δ: 2.91 (3H, s), 3.00 (2H, t), 3.56 (2H, t), 4.01 (3H, s), 4.48 (2H, s), 7.13 (1H, d), 7.23 (1H, d), 8.08 (1H, dd), 8.16 (1H, s), 8.29 (1H, s), 8.35 (1H, d); m/z ($API^+$): 463 ($MH^+$)

EXAMPLE 17

N-(8-Styryl-2-trifluroacetyl-1,2,3,4-tetrahydroisoquinolin-7-yl)-4-methoxy-3-trifluoromethylbenzamide A mixture of N-(8-bromo-2-trifluoroacetyl-1,2,3,4-tetrahydroisoquinolin-7-yl)-4-methoxy-3-trifluoromethylbenzamide (0.525 g), palladium diacetate (0.011 g), tris(o-tolyl)phosphine (0.03 g), triethylamine (0.15 g) and styrene (0.16 g) were combined in acetonitrile and warmed to reflux for 23 h. The mixture was cooled, partitioned between dichloromethane/water, the organic phase separated and solvent removed at reduced pressure. The residue was column chromatographed (silica gel, ethyl acetate/hexane mixtures as eluant) to provide the title compound (0.46 g).

$^1$H NMR ($CDCl_3$) δ: 2.99 (2H, m), 3.85 (2H, m), 3.93, 4.01 (3H, s, rotamers), 4.75 (2H, m), 6.81–7.26 (4H, m), 7.39–7.53 (3H, m), 7.92–8.40 (4H, m); m/z ($API^+$): 549 ($MH^+$)

EXAMPLE 18

N-(8-Styryl-1,2,3,4-tetrahydroisoquinolin-7-yl)-4-methoxy-3-trifluoromethylbenzamide The title compound (0.08 g) was prepared from N-(8-styryl-2-trifluoroacetyl-1,2,3,4-tetrahydroisoquinolin-7-yl)-4-methoxy-3-trifluoromethylbenzamide (0.439 g) according to the method of Example 2.

$^1$H NMR ($CDCl_3$) δ: 2.83 (2H, t), 3.12 (2H, t), 3.93 (3H, s), 3.99 (2H, s), 6.77 (1H, d), 6.94 (1H, d), 7.00 (1H, s), 7.11

(1H, d), 7.30–7.50 (5H, m), 7.93–7.99 (2H, m), 8.16 (1H, d), 8.26 (1H, s); m/z (API+): 453 (MH+)

EXAMPLE 19

N-(8-Styryl-2-methyl-1,2,3,4-tetrahydroisoquinolin-7-yl)-4-methoxy-3-trifluoromethylbenzamide hydrochloride The title compound (0.033 g) was prepared from N-(8-styryl-1,2,3,4-tetrahydroisoquinolin-7-yl)-4-methoxy-3-trifluoromethylbenzamide (0.068 g) according to the method of Example 3. The free base was converted into the hydrochloride salt by treatment of a methanol solution with excess ethereal HCl.

$^1$H NMR (CDCl$_3$) δ: 2.46 (3H, s), 2.66 (2H, t), 2.95 (2H, t), 3.52 (2H, s), 3.93 (3H, s), 6.79 (1H, d), 6.95 (1H, d), 7.00 (1H, s), 7.14 (1H, d), 7.35–7.53 (5H, m), 7.93–7.98 (2H, m), 8.20 (1H, d), 8.25 (1H, s); m/z (API+): 467 (MH+)

The following Examples were prepared using the methods described for the Descriptions, Preparations and Examples above.

EXAMPLE 20

N-(8-Bromo-2-trifluoroacetyl-1,2,3,4-tetrahydroisoquinolin-7-yl)-3-acetyl-4-ethoxybenzamide $^1$H NMR (250 MHz, CDCl$_3$) δ: 1.54 (3H, t, J=7 Hz), 2.68 (3H, s), 2.98 (21H, m), 3.87 (2H, m, restricted amide rotation), 4.25 (2H, q, J=7 Hz), 4.80 (2H, br) 7.05 (1H, d, J=8 Hz), 7.19 (1H, m), 8.04 (1H, d), 8.10 (1H, dd, J=8, 2 Hz), 8.22–8.36(2H, m) and 8.32 (1H, m); m/z (API): 537, 535 (MNa+; 100%), 515, 513 (MH+; 10%).

EXAMPLE 21

N-(8-Bromo-1,2,3,4-tetrahydroisoquinolin-7-yl)-3-acetyl-4-ethoxybenzamide $^1$H NMR (250 MHz, d$_6$DMSO) δ: 1.46 (3H, t, J=7 Hz), 2.60 (3H, s), 2.73 (2H, t), 2.93 (2H, t), 3.82 (2H, s), 4.26 (2H, q, J=7 Hz), 7.12 (1H, d, J=8 Hz), 7.28 (2H, m), 8.15 (1H, dd, J=8, 2 Hz), 8.26 (2H, s), 9.95 (1H, s); m/z (API): 419, 417 (MH+; 100%)

EXAMPLE 22

N-(8-Chloro-1,2,3,4-tetrahydroisoquinolin-7-yl)-3-fluoro-4-methoxybenzamide $^1$H NMR (250 MHz, CDCl$_3$) δ: 2.79 (2H, t,), 3.11 (2H, t), 3.97 (3H, s), 4.05 (2H, s), 7.09 (2H, m), 7.68 (2H, m), 8.28 (2H, m); m/z (API): 335.1 (MH+; 100%)

EXAMPLE 23

N-(8-Chloro-1,2,3,4-tetrahydroisoquinolin-7-yl)-3-chloro-4-ethoxybenzamide $^1$H NMR (250 MHz, CDCl$_3$) δ: 1.51 (3H, t, J=7 Hz), 2.78 (2H, t,), 3.10 (2H, t), 4.03 (2H, s), 4.18 (2H, q, J=7 Hz), 6.98 (1H, d, J=8 Hz), 7.06 (1H, d), 7.77 (1H, dd, J=8, 2 Hz), 7.94 (1H, d), 8.23 (1H, d), 8.31 (1H, s); m/z (API): 365.1 (MH+; 100%)

EXAMPLE 24

N-(8-Chloro-1,2,3,4-tetrahydroisoquinolin-7-yl)-3-bromo-4-methoxybenzamide $^1$H NMR (250 MHz, d$_6$DMSO) δ: 2.70 (2H, t), 2.91 (2H, t), 3.83 (21, s), 3.94 (3H, s), 7.10 (1H, d, J=8 Hz), 7.22–7.32 (2H, m), 8.02 (1H, dd, J=8, 2 Hz), 8.22 (1H, d, J=2 Hz), 9.98 (1H, s); m/z (API): 397, 395 (MH+; 100%)

EXAMPLE 25

N-(8-Chloro-1,2,3,4-tetrahydroisoquinolin-7-yl)-3-acetyl-4-ethoxybenzamide $^1$H NMR (250 MHz, CDCl$_3$) δ: 1.54 (3H, t, J=7 Hz), 2.68 (3H, s), 2.80 (2H, t), 3.12 (2H, t), 4.05 (2H, s), 4.24 (2H, q, J=7 Hz), 7.07 (2H, m), 8.11 (1H, dd, J=8, 2 Hz), 8.25 (2H, m), 8.37 (1H, s); m/z (API): 373.2 (MH+; 100%)

EXAMPLE 26

N-(8-Chloro-1,2,3,4-tetrahydroisoquinolin-7-yl)-3-acetyl-4-iso-propoxybenzamide $^1$H NMR (250 MHz, CDCl$_3$) δ: 1.46 (6H, d, J=7 Hz), 2.66 (3H, s), 2.78 (2H, t), 3.10 (2H, t), 4.04 (2H, s), 4.80 (1H, sep, J=7 Hz), 7.07 (2H, d, J=8 Hz), 8.10 (1H, dd, J=8, 2 Hz), 8.21 (1H, d, J=8 Hz), 8.24 (1H, d, J=2 Hz), 8.39 (1H, s); m/z (API): 409 (MNa+; 100%), 387 (MH+; 18%)

PHARMACOLOGICAL DATA

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test with pKi's greater than 6. For example, compounds of Examples 2, 3, 5, 6, 8–12, 14, 15, 18, 19 gave pKi values greater than 7.

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

1. Loscher, W. and Schmidt, D. (1988). Epilepsy Res., 2, 145–181

Method for mouse model

Mice (naive male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

2. Dixon, W. J. and Mood, A. M. (1948). J. Amer. Stat. Assn., 43, 109–126
3. Litchfield, J. T. and Wilcoxon, F. (1949). J. Pharmacol. exp. Ther., 96, 99–113

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Results

Compounds of this invention dosed at 10 mg/kg by the oral route as a suspension in methyl cellulose and tested one hour post dosing showed an increase in seizure threshold.

Method for rat model

The threshold for maximal (tonic hindlimb extension) electroshock seizures in male rats (Sprague Dawley, 80–150 g, 6 weeks old) was determined by a Hugo Sachs Electronik stimulator which delivered a constant current (0.3 sec duration; from 1–300 mA in steps of 5–20 mA). The procedure is similar to that outlined above for mouse and full details are as published by Upton et al,.[4]

4. N. Upton, T. P. Blackburn, C. A. Campbell, D. Cooper, M. L. Evans, H. J. Herdon, P. D. King, A. M. Ray, T. O. Stean, W. N. Chan, J. M. Evans and M. Thompson. (1997). B. J. Pharmacol., 121, 1679–1686

The percentage increase or decrease in $CC_{50}$ for each group compared to the control is calculated.

Drugs are suspended in 1% methyl cellulose.

Results

At a dosage of 2 mg/kg p.o. at 2 h, the compounds of Examples 2, 3, 5, 6, 8 and 9 show statistically significant increases of 120%, 160%, 320%, 260%, 400% and 340% respectively.

What is claimed is:

1. A compound of formula (I) or pharmaceutically acceptable salt or solvate thereof:

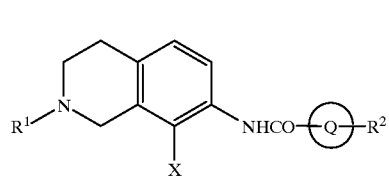

(I)

where Q is a monocyclic or bicyclic aryl or heteroaryl ring,
$R^1$ is hydrogen, $C_{1-6}$alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkylSO$_2$—,
$R^2$ is hydrogen or up to three substituents selected from halogen, $NO_2$, CN, $N_3$, $CF_3O$, $CF_3S$—, $CF_3CO$—, tifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, ($C_{1-4}$alkyl)$_2$NSO$_2$—, ($C_{1-4}$alkyl)NHSO$_2$—, ($C_{1-4}$alkyl)$_2$NCO—, ($C_{1-4}$alkyl)NHCO, $CONH_2$, $CF_3SO_2$, $C_{1-6}$alkenyl, $C_{1-6}$alkynyl or $C_{1-6}$hydroxyalkyl; or —$NR^3R^4$ where $R^3$ is hydrogen or $C_{1-4}$alkyl, and
$R^4$ is hydrogen, $C_{1-4}$alkyl, formyl, —$CO_2C_{1-4}$alkyl or —$COC_{1-4}$alkyl; or two $R^2$ groups together form a carbocyclic ring that is saturated or unsaturated and unsubstituted or substituted by —OH or =O; and
X is halogen, $C_{1-6}$alkoxy, $C_{1-6}$alkyl, $C_{2-6}$alkenyl optionally substituted by phenyl.

2. A compound according to claim 1 of formula (IA)

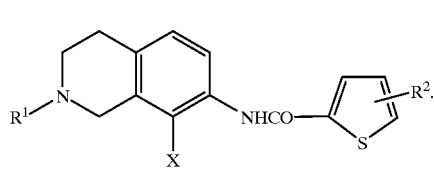

(IA)

3. A compound according to claim 1 of formula (IB)

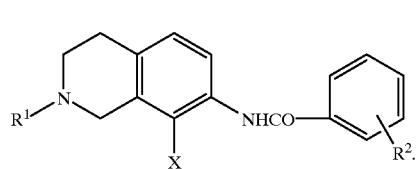

(IB)

4. A compound of claim 1 in which
$R^1$ is hydrogen, methyl, ethyl, propyl, hydroxyethyl, formyl, acetyl, trifluoroacetyl or methanesulfonyl,
$R^2$ is hydrogen or one or more of methyl, ethyl, n-butyl, iso-propyl, t-butyl, phenyl, methoxy, ethoxy, iso-propoxy, n-butoxy, cyclopropylmethoxy, phenoxy, benzyloxy, amino, acetylamino, nitro, azido, cyano, bromo, chloro, fluoro, iodo, acetyl, propionyl, pivaloyl, iso-butyroyl, benzoyl, iodobenzoyl, trifluoromethyl, perfluoroethyl, trifluoromethoxy, trifluoroacetyl, trifluoromethyldiazirinyl, methanesulfonyl, n-propylsulfonyl, isopropylsulfonyl, dimethylsulfamoyl, $CF_3SO_2$;

or two groups R² form a benzene, cyclopentane or cyclopentanone ring;

X is methyl, ethyl, chloro, bromo, iodo, fluoro, phenylethenyl.

5. A compound of claim 1 in which
R¹ is hydrogen, methyl, formyl, hydroxyethyl or trifluoroacetyl,
R² is hydrogen or one or more of methyl, ethyl, isopropyl, methoxy, ethoxy, iso-propoxy, acetyl, propionyl, pivaloyl, cyano, bromo, chloro, fluoro, iodo, trifluoromethyl,
X is methyl, ethyl, chloro or bromo.

6. A compound of formula (I) of claim 1 selected from:
N-(8-chloro-2-trifluoroacetyl-1,2,3,4-tetrahydroisoquinolin-7-yl)-3-bromo-4-ethoxybenzamide;
N-(8-chloro-1,2,3,4-tetrahydroisoquinolin-7-yl)-3-bromo-4-ethoxybenzamide;
N-(8-chloro-2-methyl-1,2,3,4-tetrahydroisoquinolin-7-yl)-3-bromo-4-ethoxybenzamide;
N-(8-chloro-2-trifluoroacetyl-1,2,3,4-tetrahydroisoquinolin-7-yl)-4-methoxy-3-trifluoromethylbenzamide;
N-(8-chloro-1,2,3,4-tetrahydroisoquinolin-7-yl)-4-methoxy-3-trifluoromethylbenzamide;
N-(8-chloro-2-methyl-1,2,3,4-tetrahydroisoquinolin-7-yl)-4-methoxy-3-trifluoromethylbenzamide;
N-(8-bromo-2-trifluoroacetyl-1,2,3,4-tetrahydroisoquinolin-7-yl)-4-methoxy-3-trifluoromethylbenzamide;
N-(8-bromo-1,2,3,4-tetrahydroisoquinolin-7-yl)-4-methoxy-3-trifluoromethylbenzamide;
N-(8-bromo-2-methyl-1,2,3,4-tetrahydroisoquinolin-7-yl)-4-methoxy-3-trifluoromethylbenzamide;
N-(2,8-Dimethyl-1,2,3,4-tetrahydroisoquinolin-7-yl)-4-methoxy-3-trifluoromethylbenzamide;
N-(2-(2-Hydroxyethyl)-8-chloro-1,2,3,4-tetrahydroisoquinolin-7-yl)-4-methoxy-3-trifluoromethylbenzamide;
N-(2-formyl-8-chloro-1,2,3,4-tetrahydroisoquinolin-7-yl)-4-methoxy-3-trifluoromethylbenzamide;
N-(8-ethyl-2-trifluoroacetyl-1,2,3,4-tetrahydroisoquinolin-7-yl)-4-methoxy-3-trifluoromethylbenzamide;
N-(8-ethyl-1,2,3,4-tetrahydroisoquinolin-7-yl)-4methoxy-3-trifluoromethylbenzamide;
N-(8-ethyl-2-methyl-1,2,3,4-tetrahydroisoquinolin-7-yl)-4-methoxy-3-trifluoromethylbenzamide;
N-(8-chloro-2-methanesulfonyl-1,2,3,4-tetrahydroisoquinolin-7-yl)-4-methoxy-3-trifluoromethylbenzamide;
N-(8-Styryl-2-trifluoroacetyl-1,2,3,4-tetrahydroisoquinolin-7-yl)-4-methoxy-3-trifluoromethylbenzamide;
N-(8-Styryl-1,2,3,4-tetrahydroisoquinolin-7-yl)-4-methoxy-3-trifluoromethylbenzamide;
N-(8-Styryl-2-methyl-1,2,3,4-tetrahydroisoquinolin-7-yl)-4-methoxy-3-trifluoromethylbenzamide;
N-(8-Bromo-2-trifluoroacetyl-1,2,3,4-tetrahydroisoquinolin-7-yl)-3-acetyl-4-ethoxybenzamide;
N-(8-Bromo-1,2,3,4-tetrahydroisoquinolin-7-yl)-3-acetyl-4-ethoxybenzamide;
N-(8-Chloro-1,2,3,4-tetrahydroisoquinolin-7-yl)-3-fluoro-4-methoxybenzamide;
N-(8-Chloro-1,2,3,4-tetrahydroisoquinolin-7-yl)-3-chloro-4-ethoxybenzamide;
N-(8-Chloro-1,2,3,4-tetrahydroisoquinolin-7-yl)-3-bromo-4-methoxybenzamide;
N-(8-Chloro-1,2,3,4-tetrahydroisoquinolin-7-yl)-3-acetyl-4-ethoxybenzamide; and
N-(8-Chloro-1,2,3,4-tetrahydroisoquinolin-7-yl)-3-acetyl-4-iso-propoxybenzamide.

7. A process for the preparation of compounds of formula (I) according to claim 1, which comprises reacting a compound of formula (II)

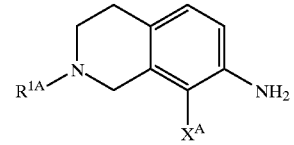

where $R^{1A}$ is $R^1$ as defined in claim 1 or a group convertible to $R^1$ and $X^A$ is X as defined in claim 1 or a group convertible to X with a compound of formula (III)

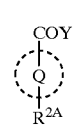

(III)

where Q is as defined in formula (I), Y is Cl or OH, and $R^{2A}$ groups are independently $R^2$ as defined for formula (I) or groups convertible to $R^2$, and where required converting an $X^A$, $R^{1A}$ or $R^{2A}$ group to an X, $R^1$ or $R^2$ group, converting one X, $R^1$ or $R^2$ group to another X, $R^1$ or $R^2$ group, converting a salt product to the free base or another pharmaceutically acceptable salt, or converting a free base product to a pharmaceutically acceptable salt.

8. A pharmaceutical composition suitable for use in the treatment and/or prophylaxis of anxiety, mania, depression, panic disorders and/or aggression, disorders associated with a subarachnoid haemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity (spasticity), temporomandibular joint dysfunction, or amyotrophic lateral sclerosis (ALS) which comprises a compound of formula (I) according to claim 1, or a pharmaceutically acceptable salt or solvate thereof, and a pharmaceutically acceptable carrier.

9. A method of treatment and/or prophylaxis of anxiety, mania, depression, panic disorders and/or aggression, disorders associated with a subarachnoid haemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity (spasticity), temporomandibular joint dysfunction, or amyotrophic lateral sclerosis (ALS) comprising administering to the sufferer in need thereof an effective or prophylactic amount of a compound of formula (I) according to claim 1, or a pharmaceutically acceptable salt or solvate thereof.

10. A compound of claim 2 in which $R^1$ is hydrogen, methyl, ethyl, propyl, hydroxyethyl, formyl, acetyl, trifluoroacetyl or methanesulfonyl, $R^2$ is hydrogen or one or more of methyl, ethyl, n-butyl, iso-propyl, t-butyl, phenyl, methoxy, ethoxy, iso-propoxy, n-butoxy, cyclopropylmethoxy, phenoxy, benzyloxy, amino, acetylamino, nitro, azido, cyano, bromo, chloro, fluoro, iodo, acetyl, propionyl, pivaloyl, iso-butyroyl, benzoyl, iodobenzoyl, trifluoromethyl, perfluoroethyl, trifluoromethoxy, trifluoroacetyl, trifluoromethyldiazirinyl, methanesulfonyl, n-propylsulfonyl, isopropylsulfonyl, dimethylsulfamoyl, $CF_3SO_2$;

or two groups $R^2$ form a benzene, cyclopentane or cyclopentanone ring;

X is methyl, ethyl, chloro, bromo, iodo, fluoro, phenylethenyl.

11. A compound of claim 3 in which $R^1$ is hydrogen, methyl, ethyl, propyl, hydroxyethyl, formyl, acetyl, trifluoroacetyl or methanesulfonyl, $R^2$ is hydrogen or one or more of methyl, ethyl, n-butyl, iso-propyl, t-butyl, phenyl, methoxy, ethoxy, iso-propoxy, n-butoxy, cyclopropylmethoxy, phenoxy, benzyloxy, amino, acetylamino, nitro, azido, cyano, bromo, chloro, fluoro, iodo, acetyl, propionyl, pivaloyl, iso-butyroyl, benzoyl, iodobenzoyl, trifluoromethyl, perfluoroethyl, trifluoromethoxy, trifluoroacetyl, trifluoromethyldiazirinyl, methanesulfonyl, n-propylsulfonyl, isopropylsulfonyl, dimethylsulfamoyl, $CF_3SO_2$;

or two groups $R^2$ form a benzene, cyclopentane or cyclopentanone ring;

X is methyl, ethyl, chloro, bromo, iodo, fluoro, phenylethenyl.

12. A compound of claim 2 in which $R^1$ is hydrogen, methyl, formyl, hydroxyethyl or trifluoroacetyl, $R^2$ is hydrogen or one or more of methyl, ethyl, iso-propyl, methoxy, ethoxy, iso-propoxy, acetyl, propionyl, pivaloyl, cyano, bromo, chloro, fluoro, iodo, trifluoromethyl, X is methyl, ethyl, chloro or bromo.

13. A compound of claim 3 in which $R^1$ is hydrogen, methyl, formyl, hydroxyethyl or trifluoroacetyl, $R^2$ is hydrogen or one or more of methyl, ethyl, iso-propyl, methoxy, ethoxy, iso-propoxy, acetyl, propionyl, pivaloyl, cyano, bromo, chloro, fluoro, iodo, trifluoromethyl, X is methyl, ethyl, chloro or bromo.

* * * * *